US008916182B2

(12) United States Patent
Van Cutsem et al.

(10) Patent No.: US 8,916,182 B2
(45) Date of Patent: Dec. 23, 2014

(54) COMPOSITION COMPRISING OLIGOGALACTURONANS AND POLYCATIONIC SACCHARIDES

(75) Inventors: Pierre Van Cutsem, Ottignies (BE); Juan Carlos Cabrera Pino, Namur (BE)

(73) Assignee: Universite de Namur, Namur (BE)

( * ) Notice: Subject to any disclaimer, the term of this patent is extended or adjusted under 35 U.S.C. 154(b) by 1305 days.

(21) Appl. No.: 12/516,776

(22) PCT Filed: Nov. 28, 2007

(86) PCT No.: PCT/EP2007/062968
§ 371 (c)(1),
(2), (4) Date: Dec. 9, 2009

(87) PCT Pub. No.: WO2008/065151
PCT Pub. Date: Jun. 5, 2008

(65) Prior Publication Data
US 2010/0087369 A1 Apr. 8, 2010

(30) Foreign Application Priority Data

Nov. 28, 2006 (EP) .................................. 06124918

(51) Int. Cl.
| A01N 43/16 | (2006.01) |
| A01N 25/00 | (2006.01) |
| C08L 5/06 | (2006.01) |
| C08L 5/08 | (2006.01) |
| C05F 11/00 | (2006.01) |
| A61K 9/14 | (2006.01) |
| A01N 43/04 | (2006.01) |
| A01N 25/02 | (2006.01) |

(52) U.S. Cl.
CPC . A01N 43/16 (2013.01); C08L 5/06 (2013.01); C08L 5/08 (2013.01); Y10S 514/97 (2013.01)
USPC ............. 424/405; 424/400; 424/488; 514/54; 514/55; 514/970; 504/292; 504/362; 71/11

(58) Field of Classification Search
USPC .............. 424/400, 405, 488; 514/54, 55, 970; 71/11; 504/292, 362
See application file for complete search history.

(56) References Cited

U.S. PATENT DOCUMENTS

| 5,474,926 A | 12/1995 | Harman et al. |
| 5,919,574 A | 7/1999 | Hoagland |
| 6,512,166 B1 | 1/2003 | Harman et al. |
| 2002/0119941 A1* | 8/2002 | Ni et al. ........................... 514/44 |

FOREIGN PATENT DOCUMENTS

| WO | WO 03/068824 A1 | 8/2003 |
| WO | WO 2005/108596 A1 | 11/2005 |
| WO | WO 2006/085075 A2 | 8/2006 |

OTHER PUBLICATIONS

J. Messiaen, N. D. Read, P. Van Cutsem and A. J. Trewavas, "Cell wall oligogalacturonides increase cytosolic free calcium in carrot protoplasts", Journal of Cell Science 104, 365-371 (1993).*
Entsar I. Rabea, Mohamed E.-T. Badawy, Christian V. Stevens, Guy Smagghe, and Walter Steurbaut, "Chitosan as Antimicrobial Agent: Applications and Mode of Action", Biomacromolecules, 2003, 4(6), 1457-1465.*
Marianne Hiorth, Anna-Lena Kjøniksen, Kenneth D. Knudsen, Sverre Arne Sande and Bo Nyström, "Structural and dynamical properties of aqueous mixtures of pectin and chitosan" European Polymer Journal 41 (2005) 1718-1728.*
Valot et al., "Identification of membrane-associated proteins regulated by the arbuscular mycorrhizal symbosis," *Plant Molecular Biology* (2005) 59: 565-580.
Beaudoin-Eagan et al., "Tyrosine and phenylalanine ammonia lyase activities during shoot initiation in tobacco callus cultures," *Plant Physiol.* (1985) 78: 438-441.
Boudart et al., "Differential elicitation of defense responses by pectic fragments in bean seedlings," *Planta* (1998) 206: 86-94.
Cervone et al., "Perception of fungal elicitors and signal transduction," *Signal Transduction in Plants* (1997): 153-177.
Grant et al., "Biological interactions between polysaccharides and divalent cations: The egg-box model," *FEBS Letters* (1973) 32(1): 195-198.
Templeton et al., "Elicitors and defence gene activation," *Plant, Cell and Environment* (1988) 11: 395-401.
Kuchitsu et al., "N-Acetylchitooligosaacharides, biotic elicitor for phytoalexin production, induce transient membrane depolarization in suspension-cultured rice cells," *Protoplasma* (1993) 174: 79-81.
Liners et al., "Influence of the degree of polymerization of oligogalacturonates and of esterification pattern of pectin on their recognition by monoclonal antibodies," *Plant Physiol.* (1992) 99: 1099-1104.
Liners et al., "Monoclonal antibodies against pectin," *Plant Physiol.* (1989) 91: 1419-1424.
Powell et al., "Conformations and interactions of pectins," *J. Mol. Biol.* (1982) 155: 517-531.
Messiaen et al., "Polyamines and pectins. II. Modulations of pectic-signal transduction," *Planta* (1999) 208: 247-256.
Harman et al., "Trichoderma and Gliocladium in biological control: an overview," *Enzymes, Biological Control and Commercial Applications* (1998), vol. 2, Chapter 6: 131-151.
Chang et al., "Swelling behavior and the release of protein from chitosan-pectin composite particles," *Carbohydrate Polymers* (2000) 43: 163-169.
Munjeri et al., "Hydrogel beads based on amidated pectins for colon-specific drug delivery: the role of chitosan in modifying drug release," *Journal of Controlled Release* (1997) 46: 273-278.

(Continued)

*Primary Examiner* — John Pak
*Assistant Examiner* — Nathan W Schlientz
(74) *Attorney, Agent, or Firm* — Merchant & Gould P.C.

(57) ABSTRACT

A 'bioactive' composition that has one or more oligogalacturonans ((1→4)-α-D-galacturonan) or any other oligosaccharides (oliguluronans) that may present an 'egg box' conformation, this conformation being further stabilized by one or more polycationic saccharide(s), preferably either a chitosan oligosaccharide or a chitosan polysaccharide. A method prepares this composition and it is used, in medical, pharmaceutical, agricultural, nutraceutical, food, feed, textile, cosmetic, industrial and/or environmental applications.

10 Claims, 7 Drawing Sheets

(56) References Cited

OTHER PUBLICATIONS

Atyabi et al., "In vitro evaluation and modification of pectinate gel beads containing trimethyl chitosan, as a multi-particulate system for delivery of water-soluble macromolecules to colon," *Carbohydrate Polymers* (2005) 61: 39-51.

Rodriguez et al., "New chitosan-calcium pectinate pellets and their adsorption capacity," *Colloid. Polym. Sci.* (2006) 285: 119-124.

Hiorth et al., "Immersion coating of pellets with calcium pectinate and chitosan," *International Journal of Pharmaceutics* (2006) 308: 25-32.

Nurjaya et al., "Effects of microwave on drug release properties of matricies of pectin," *Carbohydrate Polymers* (2005) 62: 245-257.

Dörenburg et al., "Semicontinuous process for anthraquinone production with immobilized *Cruciata glabra* cell cultures in a three-phase system," *Journal of Biotechnology* (1996) 50: 55-62.

Kauss et al., "The degrees of polymerization and N-acetylation of chitosan determine its ability to elicit callose formation in suspension cells and protoplasts of *Catharanthus roseus*" Planta, vol. 178, pp. 385-392 (1989).

Lesney, "Polycation-like Behaviour of Chitosan on Suspension-Culture Derived Protoplasts of Slash Pine", *Phytochemistry,* vol. 29, No. 4, pp. 1123-1125 (1990).

Pospieszny et al., "Ultrastructure of Leaf Cells Treated with Chitosan", Institute of Plant Protection, Department of Virology and Bacteriology, pp. 139-144 (1997).

Tiuterev et al., "Chitosan: Mechanism of Action and Ways of Using as Ecologically Safe Means in Enhancement of Plant Disease Resistance", *Arch. Phytopath Pflanz,* vol. 30, pp. 323-332 (1996).

Vander et al., "Comparison of the Ability of Partially N-Acetylated Chirosans and Chitooligosaccharides to Elicit Resistance Reactions in Wheat Leaves", Plant Physiol, vol. 118, pp. 1353-1359 (1998).

\* cited by examiner

COMPOSITION COMPRISING OLIGOGALACTURONANS AND POLYCATIONIC SACCHARIDES

This application is a National Stage Application of PCT/EP2007/062968, filed Nov. 28, 2007, which claims benefit of Ser. No. 06124918.1, filed Nov. 28. 2006 in the EPO and which application(s) are incorporated herein by reference. To the extent appropriate, a claim of priority is made to each of the above disclosed applications.

FIELD OF THE INVENTION

The present invention is related to a "bioactive" composition that comprises one or more oligogalacturonans (($1\rightarrow4$)-α-D-galacturonan) or any other oligosaccharides (oligoguluronans) that may present an "egg box" conformation, this conformation being further stabilized by one or more polycationic saccharide(s), preferably either a chitosan oligosaccharide or a chitosan polysaccharide.

The present invention is also related to a method for the preparation of this composition and its use, in medical, pharmaceutical, agricultural, nutraceutical, food, feed, textile, cosmetic, industrial and/or environmental applications.

BACKGROUND OF THE INVENTION

Pectin and Pectin Fragments

Natural polysaccharides, such as starch, cellulose, chitin, alginate and pectin are of great technological importance because they are available in great amounts and they present specific characteristics usually not present in synthetic polymers.

Pectin constitutes a dense molecular network that accounts for much of the mechanical properties of plant cell wall.

Hairy regions of pectins (Rhamnogalacturonan) coexist with smooth homopolygalacturonic (galacturonan) domains that can dimerize according to the so-called "egg-box model" (Grant, FEBS letters, volume 32, p. 195-198, 1973). By circular dichroism, the existence of this "egg-box" conformation of interchain chelation of calcium has been confirmed (POWELL et al. Journal of Molecular Biology vol. 155, p. 517-531, 1982).

The extent of such junction zones in the cell wall depends largely on the charge density of the polyanion, the availability of divalent cations and is inhibited by methylesterification and acetylesterification (Liners et al. Plant Physiology vol. 90, p. 1090 1104, 1992).

Pectin is also a privileged target involved in morphological processes and in host-pathogen interactions. Pectolytic enzymes release oligogalacturonans that can modulate different physiological processes within the cell wall matrix and the protoplast.

It is also known that at different concentrations these oligogalacturonans may modify the biological activity of the cells.

Therefore, these oligogalacturonans are suitable for the treatment of plants, especially in growing and protecting plant methods based upon the use of these natural products. More particularly, these oligogalacturonans are suitable for the induction of increased innate plant defenses against pathogens.

Van Cutsem and Messiaen (Planta, vol. 208. p. 246-256, 1999) describe the adsorption of polyamines upon polygalacturonic acid in the presence of competing mono and divalent cations ($Na^+$, $Ca^{2+}$). Among polyamines, putrescine, spermidine and spermine were tested. The authors show that signal transduction cascade initiated in plant cells by $Ca^{2+}$ bound ($1\rightarrow4$)-α-D-oligogalacturonan was blocked by spermidine and spermine, but not by putrescine. It is hypothesized that disruption by spermidine and spermine of the $Ca^{2+}$ induced supra molecular conformation of pectic fragments was the cause of the inhibition of the pectic signal. Therefore, it seems that polyamines can act on plant cell physiology by modulating the transduction of the pectic signal. Others oligosaccharides such as alginate may present this "Egg-Box" conformation and can act on plant physiology.

Chitin and Chitosan

Chitin is a natural high molecular weight polymer widely found in nature (second major biopolymer after cellulose) and is the main component of insects and crustacean cuticle. Chitin is also part of the cell walls of some fungi and other organisms. Chitosan is produced at the industrial level by chemical modifications of chitin and is also naturally found in a few organisms.

Chitosan is the random copolymer of N-acetyl (D)-glucosamine and (D)-glucosamine. The international patent application WO 03/068824 describes the chemical structure of chitosan and various methods for obtaining this chitosan. Furthermore, this patent application also describes a method for isolating cell wall derivatives from fungal and yeast biomass and a method for obtaining chitosan from this method. This patent application also describes the use of chitosan in medical, pharmaceutical, agricultural, nutraceutical, food, textile, cosmetic, industrial and/or environmental applications.

However, chitosan still presents several drawbacks, such as the high concentrations needed to obtain a physiological effect (over 1 g per liter) and could be toxic at such high concentrations.

Pectin and Chitosan Combinations

U.S. Pat. No. 5,919,574 describes biodegradable laminated films fabricated from pectin and chitosan. This patent states that the cationic property of chitosan offers an opportunity to take advantage of electrostatic interactions with anionic partially demethylated pectin. The inventors of this patent state that there is a combination of hydrogen bonding and electrostatic forces between carboxylate groups of pectin and protonated amino groups of chitosan and that the compatible water activity makes possible a stable interface between a pectic film and a chitosan film. This patent also describes the use of the obtained laminated films in a number of applications, including medical applications (production of patches, biodegradable pouches or bags, encapsulation of living cells, etc).

The international patent application WO01/82724 describes a composition containing aminopolysaccharides and negatively charged polysaccharides. Among the tested amino polysaccharides, the inventors describe chitosan and chitosan derivatives combined with negatively charged polysaccharides, such as pectin.

However, none of these documents describes that it is possible to improve the bioactivity of pectin fragments (oligogalacturonans). Neither do they describe any effect of chitosan molecules on calcium-induced bioactive conformation of galacturonan. More particularly, none of these documents describes either an elicitor or a fertilizer effect for a combination of pectin and chitosan fragments.

It is known that plant production is classically achieved by the use of synthetic chemicals which are not always environment friendly and are usually expensive.

Therefore, the use of these natural products could reduce the amount of crop protection or fertilizer chemicals applied to crops, allowing suitable organic agriculture and minimizing the environmental impact of agriculture.

Over the last decades, sales of organic products have shown an annual increase of at least 20%. The fastest growing sector of agriculture in retails of organic food and beverages were approximately 12.8 billions dollars. Organic food is also gaining international acceptance within nations, like Japan and Germany, becoming important international organic food markets.

AIMS OF THE INVENTION

A first aim of the present invention is to provide a composition comprising galacturonans with improved properties, such as a stabilized egg box conformation preferably detectable by the 2F4 antibody (F. LINERS, J.-J. LETESSON, C. DIDEMBOURG and P. VAN CUTSEM (1989) Monoclonal antibodies against pectin: recognition of a conformation induced by calcium. Plant Physiol. 91, 1419-1424), especially improved bioactivity properties for the growing and the protection of plants.

Another aim of the present invention is to propose a composition made of natural products.

A further aim of the present invention is to provide a composition which presents new properties for oligogalacturonans, and which could be used in medical, pharmaceutical, nutraceutical, food, textile, cosmetic, industrial and/or environmental applications.

SUMMARY OF THE INVENTION

The present invention is related to a composition comprising one or more oligogalacturonans (preferably (1→4)-α-D-oligogalacturonan), oligoguluronans (such as oligomers of alginate) or any oligomers that may present an "egg-box" conformation (with the addition of one or more cations ($Ca^{2+}$, $Na^+$ ...)), this conformation being preferably detected by 2F4 antibody and is advantageously further stabilized by (the addition of) one or more polycationic saccharide(s). A polycationic saccharide means a saccharide having multiple positive charges, preferably at least 6 (six) charges.

Advantageously, these saccharides are natural products (different from a synthetic polymer or oligomer) which means that they can be obtained from natural renewable source with little or no modifications.

Advantageously, the polycationic saccharide is an oligo- or a polysaccharide, preferably a chitosan oligosaccharide or chitosan polymer. More preferably, the chitosan oligo- or polysaccharides used have a degree of acetylation lower than 50%, preferably comprised between 0 and about 50% and a degree of polymerization higher than 5 (five).

Furthermore, the oligogalacturonans present in the composition according to the invention preferably have a degree of polymerization (DP) higher than 8 (eight), preferably comprised between 9 (nine) and 20 (twenty) or between 9 (nine) and 15 (fifteen).

The inventors have discovered unexpectedly that such composition is characterized by a synergistic effect which means that it improves the oligogalacturonans and/or possibly oligoguluronans (e.g., alginate oligomers) or others oligosaccharides characteristics (especially agronomic properties), but also reduces possible side effects of polycationic saccharides, especially if these polycationic saccharides are chitosan oligosaccharides or chitosan polymers. In particular, such composition unexpectedly reduces possible toxic properties of chitosan molecules and therefore controls and reduces cell death (induced by these chitosan molecules at high concentration).

This composition increases synergistically the bioactivity of each oligosaccharide and combines their individual potentiating effects in various fields, including medical, pharmaceutical, agricultural, nutraceutical, food, feed, textile, cosmetic, industrial, textile or paper production and/or environmental applications. This composition could be bound to a solid support surface through a covalent or non-covalent link.

In particular, this composition is an elicitor composition that could be used to protect plants (increase natural plant defense against pathogens) and to stimulate plant growth and differentiation. Elicitation can be explained as mechanism(s) by which cells and tissues of essentially all organisms respond and adapt to changes in external environmental conditions. In many cases, these mechanisms use the pathways of specific receptors for particular chemicals. When such chemicals come into contact with cell surfaces, they bind specifically to particular receptors. This binding triggers a cascade of events within the cells, including up- and down-regulation of genes and activation or repression of specific pathways within the cells. Those processes result in substantial changes in cellular physiology. Thus, these elicitors are triggers of dramatic physiological responses. Moreover, a very small quantity of the elicitor molecule is often sufficient to cause major changes in cellular physiology. An example of elicitor-based activity includes induction of immune or resistance responses in plants or animals.

The earliest response to elicitors is indicated by changes in membrane permeability and activation of specific ion channels leading to the influx of $Ca2+$ and $H+$ and the efflux of $Cl-$ and $K+$ (Cervone et al., (1997)"Perception of fungal elicitors and signal transduction" In Aducci P, ed. Signal transduction in plants Basel, Switzerland: Birkhaüser Verlag, 153-177). This step is also characterized by rapid changes in transmembrane potential. In numerous cases, depolarization of the membrane was noted (Kuchitsu et al., (1993) "N-acetylchitooligosaccharides, biotic elicitor for phytoalexin production, induce transient membrane depolarization in suspension-cultured rice cells" Protoplasma 174, 79-81). These membrane-located effects are followed by the oxidative burst, the synthesis of phytoalexins, and the activation of defense genes (Templeton and Lamb, (1988) "Elicitors and defense gene activation" Plant, Cell and Environment 11, 395-401). In the past, problems have been encountered with existing approaches to stimulate resistance as a practical method of disease control. These problems have included phytotoxicity (yellowing, necrosis, and general plant malaise), lack of significant levels of disease control, and lack of reproducibility/sustainability. The composition of the present invention advantageously alleviates these limitations.

Additionally, this composition is a fertilizing composition that could be used to increase, e.g., yields of plants, through increased height, thickness (of stem, leaves, roots ... ), biomass, or number of flower/fruit per plant. A measure of "biomass," which is basically the density or amount of plant-life, is known to be directly related to crop yield.

However, the composition according to the invention may also comprise other elements, such as other oligosaccharides, growth regulators (or growth factors), minerals, ions, nutriments, food additives, flavorings, colors, vitamins, minerals, fragrances, phyto-nutrients and other bioactive molecules for improving the bioactivity of the composition, especially the bioactivity of each oligosaccharide in these various applications.

Therefore, the composition according to the invention corresponds to a pharmaceutical composition, (including a vaccine), an adjuvant, a cosmetic composition, a food or feed composition (including functional food or functional feed), a food additive, a beverage (especially wine, beer or fruit juice) or an adjuvant to a beverage, a phytosanitary product, (preferably a fungicide composition), a fertilizer, an elicitor, or an adjuvant of these products.

For instance, the composition according to the invention could be used for recovering from said beverage, organic particles, microorganisms, colloids, proteins, heavy metals, residual pesticides, mycotoxins and endotoxins.

The composition according to the invention could also be used as natural food additives for obtaining anti-microbial and anti-fungal activities against a wide range of fungi, (including yeast) and bacteria and could also be used as adjuvant for conventional food preservatives and anti-browning agents, as component for gas permeable edible films suitable for fruit/vegetable storage, as thickening, stabilizing or emulsifying agent, as thixotropic agents or as natural flavor extender. It can also be used in various feed processes, as it may, for instance, be applied as foaming agent, as thickener or as stabilizer.

The anti-microbial and anti-fungal activity (for the protection of plants seeds or fruits) of the composition according to the invention can be used in the food or feed industry for obtaining extended shelf life, delayed ripening and decay of fruits or vegetables, for the preservation of meat, crustacean (oysters), fruits, vegetables and finished products, possibly in combination with conventional preservatives (sulphite or sodium benzoate) or as alternative to these preservatives.

The composition according to the invention can also be applied upon textile fibers in the form of a film or by impregnation of this fiber or tissue with a solution comprising the composition according to the invention. Therefore, the property of the fiber of a textile may be modified (improved antibacterial and/or antifungal properties). This textile may also correspond to medical textile for the treatment of wounds.

The cosmetic applications of the composition according to the invention are particularly suitable for skin care formulation (cream, lotion) or for the hair care formulation (as sprays, shampoos or after-shampoos formulation), in make-up composition or in tooth pastes and can also be used for their anti-UV properties, in the preparation of deodorants, in compositions of oral hygiene and in compositions for encapsulation of pigments. Advantageously, due to its non-animal origin, it is possible to use the composition without inducing the risks of allergies.

In environmental applications, the composition according to the invention could be used as a chelating agent (chelating of heavy metal) or for the treatment of waste water, especially in water purification techniques for segregation of organic compounds and heavy metals. They can be also used for precipitating certain waste compounds or other pollutants, like DDT and polychlorobenzenes or for fixing radicals.

Advantageously, the composition according to the invention could also be used in manufacturing process of paper. They can replace some amino substituents such as gum or polysynthetic polysaccharides and are suitable for reducing the use of chemical additives and for improving outputs.

It is also possible that the paper obtained by the use of the composition according to the invention may present a smoother surface and better resistance to moisture. They can also be used for the production of sanitary paper, packing paper and paperboard.

Another advantageous application of the composition according to the invention is in the field of medicine and pharmaceutical application.

Due to these good bio-adhesion properties, the composition according to the invention could be applied as anti-adhesive surgical aid, to prevent adhesion between tissues during surgery and as adjuvant for vaccines, thanks to a good mucoadhesion.

The present invention is therefore also related to any biomaterial which comprises the composition according to the invention for specific medical, diagnostic or research applications of compounds to be released in the intestines, due to the non-digestion of the composition of the invention in the stomach (delayed release).

The present invention can be formulated as an additive for oral and parenteral controlled release application and can also improve the efficacy of oral carriers by chemical modifications and binding of drugs and other bio-functional molecules and can also be used for improving films and gels forming properties of known compounds and can be used for manufacturing transdermal membranes.

Its mucoadhesive properties can also be used for obtaining a good contact with skin layers and for improving innovative drugs delivery system through local and systemic administration. They can also be used in the making of excipients in the formation of tablets, the granulation of powders, the preparation of emulsions, as wetting and coating agents. One can also use its various advantageous characteristics, such as its bioadhesiveness and its ability to form complexes (anionic, cationic or amphiphilic) drugs and polymers in drug system for improving the solubility of poorly water soluble drugs, for enhancing absorption of drugs across mucosal tissues and for potentiating (improve or modulate) immunological response of vaccines (as adjuvants of vaccines).

The known pharmaceutical properties of chitosan, especially in wound healing allow the use of the composition to prevent or to treat the formation of fibrin bits in wounds, to prevent the formation of scars and to support cell regeneration.

The composition can also be used for tissue engineering, cell transplantation and cell encapsulation. It may be used in air-permeable films, to support cellular regeneration, while protecting tissue from microbial aggressions, to form sutures and bandages, for the manufacturing of artificial skin, in systems for reconstruction of tissues and organs and/or the transplantation of cells (possibly bio (degradable) sutures and bandages).

Therefore, these pharmaceutical applications, could be advantageously combined with known compounds, for tissue repairs, such as biomaterials containing bones particles or cartilages particles, ions and salts, growth factors and hormones and plasma derivatives, such as fibrinogen, coagulation factors, platelets, including platelets rich plasma and platelets poor plasma (PRP and PPP), antibiotics, vitamins, differentiation factors, cytokines, interferons, soft tissues proteins (such as cartilages, elastin, fibrin, or their precursors), etc.

The composition according to the invention presents advantageous hydrating characteristics, wound healing properties, regenerating properties and anti-microbial and/or anti-fungal properties.

The composition according to the invention could be presented in various forms, especially liquid form (e.g., aqueous solutions), particles form (nanoparticles, microspheres, and suspensions or emulsion thereof, pellets), and porous or nonporous solid form. When considering the agricultural and agrochemical applications of the present composition, it will typically contain additional components known to be useful for applying materials to growing crops, such as one or more carrier materials, buffer materials for pH control, and the likes. Water will often be used as a carrier, but other conventional carriers may also be used. It will be appreciated that the amount of solution required for treatment of the crop will depend on the particular crop being treated. Such amount is one that is readily ascertained by a person skilled in the art.

The composition according to the invention could be also easily applied in agricultural and agrochemical systems, as a preservative coating and biostatic agent when applied on fruits, vegetables and crops, as a fertilizer, as an agent increasing the number of useful soil microorganisms and decreasing harmful ones ("biological control"). Biological control means the reduction of the amount of inoculum or disease-producing activity of a pathogen accomplished by or through one or more organisms other than man (Harman et al., "Enzymes, Biological Control and Commercial Applications," *Trichoderma* and *Gliocladium* Vol. 2, Chap. 6 (1998)). Biological control strains are known in the art and are effective in a great variety of habitats and against an assortment of pathogens (Harman et al., see above). Examples of biological control organism may be any of those identified as useful for biological control of plant disease, including, without limitation, those from following genera: *Trichoderma, Gliocladium, Pythium, Phytophthora, Rhizoctonia, Fusarium, Botrytis*, and *Sclerotinia* (Harman et al., see above, and U.S. Pat. Nos. 5,474,926 and 6,512,166). Plant seeds may be soaked in aqueous solutions of the composition according to the invention to prevent fungal and/or microbial infections and increase plant production. The composition of the invention can be also used for obtaining an efficient coating of seeds.

In suitable concentrations, the composition of the invention can be used to trigger plant defense mechanisms against parasitic infections and aggressions (elicitor effect) through systemic and/or topical applications. Such an elicitor effect can be measured trough certain enzymatic activities induced in the plants treated with the composition of the invention, such as glucanase, chitinase and Phenylalanine Ammonia Lyase (PAL) activities.

In addition to its elicitor, biostatic, fertilizer, and/or preservative properties, the composition according to the invention could be used to reinforce plant roots and to thicken plants stem. The composition of the invention can also be used as phytohormone replacement, enhancement or modulator.

The composition of the invention can be used also to stimulate the synthesis of protective agents by the plant itself, to accelerate germination and the growth of plants. Examples of protective agents synthesized by plants are Nitric Oxide (NO), Reactive Oxygen Species (ROS), salicylic acid, jasmonic acid, Pathogenesis Related Proteins, and phytoalexins.

The composition according to the invention can be applied to the seeds, leaves, flowers/fruits and/or roots of the plants by spraying, drenching, soaking, dipping, injection and via fertigation systems. As a fertilizer, the composition of the invention can be indifferently applied through soil feeding or foliar feeding in order to accelerate germination and the growth of plants. The composition of the invention may be spread under a dry form or as a dilution of a solution. As an elicitor, the desired composition of the present invention may be applied in the form of a spray, or as a solid, wherein the elicitor is present together with an agriculturally acceptable adhesive carrier, e.g., methyl cellulose or Arabic gum, and applied as a powder. Application of the formulation can be carried out in accordance with techniques well known to persons skilled in the art such as by preparing a spray for application to the growing crop. It will be appreciated that the amount of solution required for treatment of the crop will depend on the particular crop being treated. Such amount is one that is readily ascertained by a person skilled in the art.

The concerned plants are dicots and monocots, preferably economically important plants selected from the group consisting of tomatoes, carrots, cucumbers, peas, lettuces, capsicums, sugar beets, potatoes, wheat, corn, rice, alfalfa, barley, rye, cotton, sunflower, peanut, sweet potato, bean, chicory, endive, cabbage, Brussels sprout, parsnip, turnip, cauliflower, broccoli, radish, spinach, onion, garlic, eggplant, pepper, celery, squash, pumpkin, zucchini, apple, pear, melon, citrus, strawberry, grape, raspberry, pineapple, soybean, tobacco, sorghum, and sugarcane. Examples of suitable ornamental plants are: *Saintpaulia*, petunia, pelargonium, poinsettia, chrysanthemum, carnation, zinnia, and turfgrasses.

The composition of the invention can be used also for obtaining a coating of known phytosanitary products such as fungicides, pesticides, herbicides, etc. Due to its improved characteristics, it can be used for obtaining a decrease in the amount of pesticides usually used for the treatment of these plants.

The advantageous adhesive characteristics of the composition according to the invention also allow its use in other fields (chemistry, metallurgy, electronics, textile, etc. . . . ) for the coating of solid supports.

Another aspect of the present invention is related to the preparation process of the composition according to the invention, wherein a sufficient amount of one or more polycationic saccharide is added to oligogalacturonans (or any other suitable oligosaccharides (oligoguluronans) that may present an "egg-box" conformation). This sufficient amount is advantageously defined according to the concentration of the oligogalacturonans (or the said others oligosaccharides) initially present and in the degree of polymerization of these saccharides.

In the preparation process of the composition according to the invention, the various elements are mixed as long as a uniform aqueous solution is obtained, i.e., no formation of polymers or gel is observed. Additionally, the pH of the composition is preferably maintained between about 5.0 and about 6.0 (for obtaining an efficient solubility of the component and for maintaining safety of the treated plant), when applicable. The composition of the invention can be prepared by, e.g., diluting a stock solution in water or any other appropriate solvent, or by mixing a solid form of the composition in water or any other appropriate solvent. The compositions so prepared are suitable for delivery through topical or systemic routes of administration.

For this preparation process a suitable amount of ions is also present for obtaining this egg-box conformation preferably detectable by the 2F4 antibody. As the different elements contain monovalent and divalent ions, in a divalent/monovalent molar ratio, preferably between about 1/50 and about 1/300 (or about 1/25 and About 1/250 milliEquivalent), they can be used to obtain the bioactive "egg-box" conformation of these oligogalacturonans (or others oligosaccharides) further stabilized by the addition of these polycationic saccharides. The ratio of divalent/monovalent cations can be decreased in non-physiological conditions (such as ELISA) or increased in physiological conditions (such as cell cultures) where, e.g., a high $Na^+$ concentration would be detrimental. $Ca^{2+}$ is preferably used as divalent ion. Other divalent cations are also suitable ($Mn^{2+}$, $Zn^{2+}$, $Cu^{2+}$ . . . ).

For oligogalacturonans that present high degrees of polymerization (higher than 8) a higher amount of polycationic saccharides is added. This concentration is also defined according to the number of positive charges present in the polycationic saccharides.

This concentration is characterized by the degree of polymerization of the added polycationic saccharides. Preferably, the added oligosaccharides have a degree of polymerization higher than 5.

Advantageously, the amount of the two components is defined according to the characteristics of the composition to be obtained, preferably for obtaining an efficient stabilization required by the "egg-box" conformation which is preferably characterized by its capacity to bind to the specific (Mouse Ig G1) antibody PP-2F4 sold by the company plantprobes (UK) (www.plantprobes.co.uk).

Another aspect of the invention is related to the ageing of the mixture in order to increase the proportion of galacturonan molecules in the bioactive conformation as exemplified below.

Alginate saccharides (oligoguluronans) bind $Ca^{2+}$ ions in a co-operative process, which has also been explained according to the <<egg-box model>>. One may stabilize these alginate egg boxes with the chitosan oligosaccharides or other polycationic polymers (polyamines or polycationic saccharides).

Another aspect of the present invention is related to the use of this composition in the above mentioned application, especially in medical, pharmaceutical, nutraceutical, food, feed, textile, cosmetic, industrial, agronomic and/or environmental applications, especially in applications where the synergistic effect of the two components of the composition is observed or in applications wherein the possible drawbacks of one or both individual component(s) are reduced; for instance, for modulating cell death induced by individual component, for obtaining a reduction of the oxidative stress reaction induced by addition of individual component (e.g., for obtaining lower accumulation of reactive oxygen species, such as hydrogen peroxide) and for obtaining an increased activity in cell systems (such as phenylalanine ammonia lyase activity involved in the defense against biotic stresses induced by pathogens).

Yet another aspect of the present invention is a method of increasing resistance of plants to diseases. This method involves applying a composition of the present invention to plants under conditions effective to increase the resistance of the plant to diseases. Application of the desired composition of the present invention is carried out as described above, using a sufficient amount of the desired composition of the present invention appropriately prepared for the selected mode of application.

A further aspect of the present invention is a method of increasing the yields of plants, through increased height, thickness (of stem, leaves, roots . . . ), biomass, or number of flower/fruit per plant. This method involves applying a composition of the present invention to plants under conditions effective to obtain higher yields. Application of the desired composition of the present invention is carried out as described above, using a sufficient amount of the desired composition of the present invention appropriately prepared for the selected mode of application.

DETAILED DESCRIPTION

The present invention will be described in more details in the enclosed examples, in reference to the enclosed figures which are presented as a non-limiting illustration of the various embodiments of the present invention.

EXAMPLES

Example 1

Preparation of Chitooligosaccharides

Chitosan at about 10.0 g/L concentration was dissolved by overnight shaking at room temperature in about 0.175 M acetate buffer pH about 5.5. This chitosan solution (about 90 mL) was mixed with 10 mL of Pectinex Ultra SPL (Novozymes A/S, Bagsvaerd, Denmark). The reaction mixture was incubated at about 37° C. for about 24 h. The chitooligosaccharides are isolated by selective precipitation in methanol 90% of the neutralized chitosan hydrolyzate. The composition of the chitooligosaccharide set obtained is presented in Table 1.

TABLE 1

Assigned ion composition of MALDI-TOF-MS spectra of chitooligosaccharides with degrees of polymerization (DP) of 6 or higher prepared by enzymatic hydrolysis and fractionated by selective precipitation in 90% methanol.

| m/z | Ion composition | Types |
|---|---|---|
| 1007.4 | $(GlcN)_6$ | $[M + Na]^+$ |
| 1023.4 | | $[M + K]^+$ |
| 1049.9 | $(GlcN)_5$-GlcNAc | $[M + Na]^+$ |
| 1109.9 | $(GlcN)_3$-$(GlcNAc)_3$ | $[M + H]^+$ |
| 1168.4 | $(GlcN)_7$ | $[M + Na]^+$ |
| 1184.4 | | $[M + K]^+$ |
| 1210.7 | $(GlcN)_6$-GlcNAc | $[M + Na]^+$ |
| 1226.4 | | $[M + K]^+$ |
| 1270.7 | $(GlcN)_4$-$(GlcNAc)_3$ | $[M + H]^+$ |
| 1329.5 | $(GlcN)_8$ | $[M + Na]^+$ |
| 1345.5 | | $[M + K]^+$ |
| 1371.8 | $(GlcN)_7$-GlcNAc | $[M + Na]^+$ |
| 1387.5 | | $[M + K]^+$ |
| 1490.5 | $(GlcN)_9$ | $[M + Na]^+$ |
| 1506.5 | | $[M + K]^+$ |
| 1532.8 | $(GlcN)_8$-GlcNAc | $[M + Na]^+$ |
| 1651.6 | $(GlcN)_{10}$ | $[M + Na]^+$ |
| 1812.7 | $(GlcN)_{11}$ | $[M + Na]^+$ |

Example 2

Preparation of Oligogalacturonans

Figure 1:
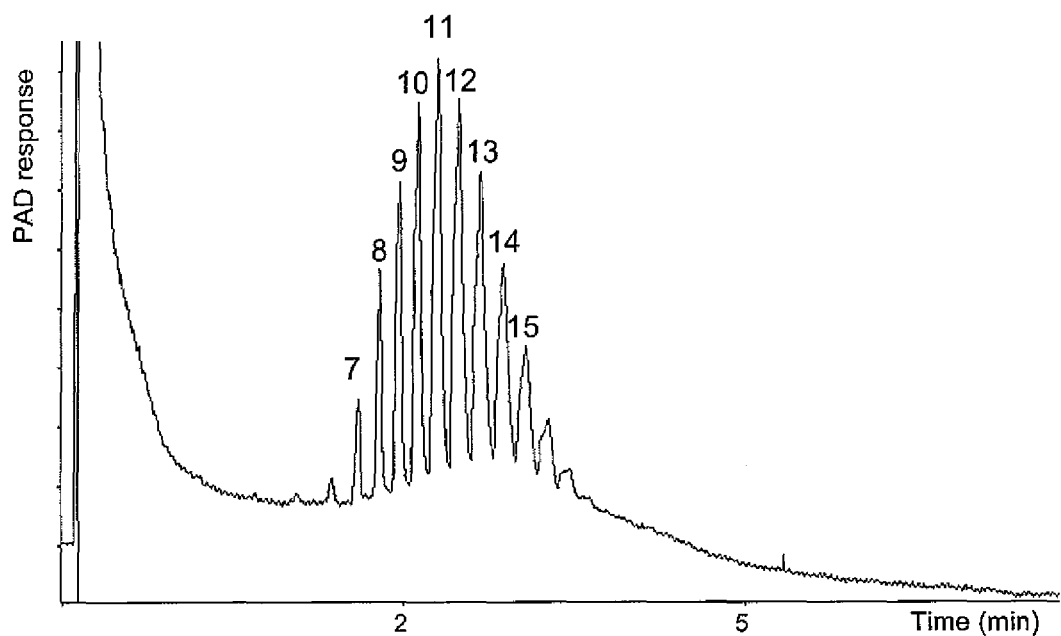
FIG. 1 is a representation of pulsed amperometric detection response versus time for the oligogalacturonan set obtained in Example 2.

Pectic oligomers were obtained by enzymatic hydrolysis of polygalacturonic acid. PGA solution (about 2% w/v, pH 6.0, 90 mL) was hydrolyzed with about 10 mL of (1:3000) Pectinex Ultra SPL solution during 60 min. After the solution had been boiled for about 10 min, the pectic oligosaccharides were fractionated by selectively precipitation of their barium salt. The composition of the oligogalacturonan set obtained is presented in FIG. 1 which is a HPAEC-PAD elution pattern of the oligogalacturonans mixture from the pectic hydrolyzate. Peaks are labeled as their corresponding degree of polymerization.

Example 3

Eggbox Conformation Stabilization

Chitooligosaccharides are able to stabilize the egg box conformation of the oligogalacturonans induced by calcium ions. This effect depends on the chitooligosaccharide degree of polymerization, degree of acetylation (DA) and chitooligosaccaride/galacturonic acid molar ratio in the mixture. A monoclonal antibody (called 2F4), which recognizes the calcium-induced egg-box conformation of pectin was used.

Microwells coating with anti-mouse immunoglobulin: Fifty μL of anti-mouse immunoglobulin (Whole molecule, SIGMA) (about 0.05 mg/mL in 50 mM carbonate buffer pH 9.5) were dispensed into each well of NUNC High Binding Capacity microplates (MAXISORP) and left overnight at 4° C. Non-specific binding was blocked by incubating the wells for about 2 h at about 37° C. with about 250 μL of albumin from bovine serum (about 30 mg/mL prepared in 50 mM acetate buffer pH 5.7 containing about 0.5 mM $CaCl_2$ and about 150 mM NaCl). This solution, when expressed in milliEquivalents, corresponds to 1 milliEquivalent calcium, since calcium is a divalent cation and 150 milliEquivalent sodium since sodium is a monovalent cation. After removal of the excess albumin, competitive solutions were added to the wells.

Preparation of Competitive Solutions and Incubation with antibodies: competitive solutions were prepared with 100 μL of 2F4 ascites diluted 177 times in the acetate buffer containing the $Ca^{2+}/Na^+$ solution described above and preincubated with about 100 μL of the mixture solution of pectic material and chitooligosaccharides during about 30 minutes at about 25° C. These oligosaccharides-antibody mixtures were then centrifuged for about 10 minutes at about 7500 g before dispensing the supernatants in microwells coated with anti-mouse immunoglobulin and blocked as described above. The microplates containing supernatants of the competitive assays were incubated during about 60 minutes at about 37° C. The microplates were then washed eight times with the buffer containing the $Ca^{2+}/Na^+$ solution as described above and further containing about 0.1% of Tween 20 before addition of about 50 μL of horseradish peroxidase-labeled sheep anti-mouse immunoglobulin (about 1:5000 in 50 mM acetate buffer containing the $Ca^{2+}/Na^+$ solution described above) for 60 minutes at 37° C. After a second washing cycle, the binding of the antibodies was revealed by about 100 μL of enhanced K-blue TMB substrate (Neogen Corporation, Lexington, Ky., USA) incubated about 20 minutes in dark at room temperature. The revealing process was stopped by about 50 μL of 1N HCl. The absorbance of the solution was measured after 15 minutes with a Titertek Multiscan® at 405 nm.

Figure 2:
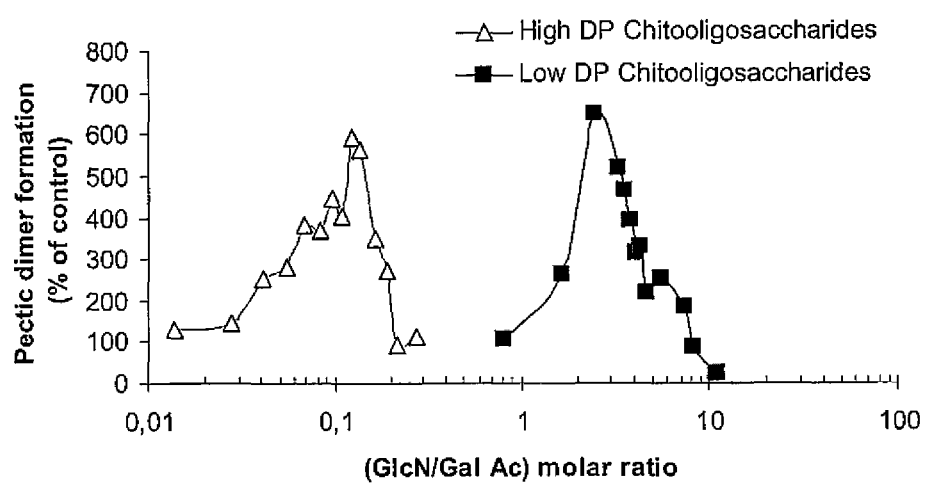
FIG. 2 is a representation of stabilization of calcium induced oligogalacturonans dimerization by chitoligosaccharides of low DA and difference degrees of polymerization.

FIG. 2 represents the stabilization of calcium induced oligogalacturonans (DP9-DP15) dimerization by chitooligosaccharides of low DA and different degrees of polymerization. The 2F4 MoAbs were incubated with oligogalacturonans and different concentrations of chitooligosaccharides with DA-10% of low and high DP. The resulting mixtures were centrifugated and the supernatants dispensed in antimouse Ig-coated microwells. Results are expressed as percentage of the absorbance of the control without chitooligosaccharides.

Example 4

In Vitro Experiments

A. Pectic molecules hinder cell death induced by high concentrations of fully deacetylated chitooligosaccharides in *Arabidopsis thaliana* cell suspensions. Cell viability is expressed as a function of protein content of the cells (mg of protein/Fresh Weight (FW)).

Figure 3:
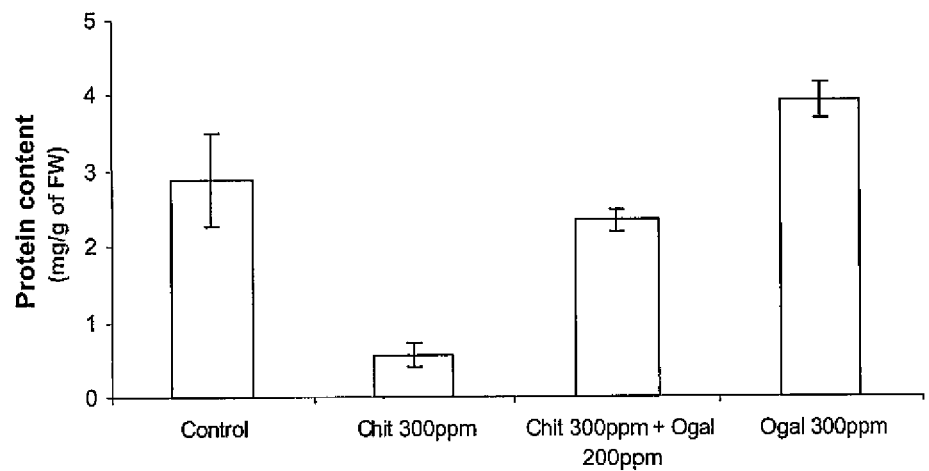
FIG. 3 is a representation of protein content of Arabidopsis cell suspensions 24 h after treatment with chitooligosaccharides oligogalacturonans and their combination.

FIG. 3 represents the protein content of *Arabidopsis* cell suspensions 24 h after treatment with chitooligosaccharides (fully deacetylated, DP between 5 and 9), oligogalacturonans (DP higher than 8) and their combination. Data are mean±SD of triplicate samples from one representative of two independent experiments.

Suspension-cultured cells derived from leaves of *Arabidopsis thaliana* strain L-MM1 ecotype *Landsberg erecta* were grown in Murashige and Skoog medium (about 4.43 g/L) with sucrose (about 30 g/L) and about 0.5 μg/mL of NAA and about 0.05 μg/mL of Kinetin, pH 5.7. Cultures were maintained under a 16 h/8 h light/dark photoperiod, at about 25° C., on a rotary shaker at 100 rpm. Cells were diluted 10-fold in fresh medium every 7 days.

Chitooligosaccharides to be tested were dissolved in 250 μL distilled water, filtered through a 0.22 μm membrane filter (MILLIPORE) and aseptically added to about 10 mL of 3 days-old-suspension-cultured cells and incubated about 24 hours at about 25° C. under mild agitation. Five mL of the reaction mixture was centrifuged for about 5 min at about 100 g and about 4° C. to collect the cells. Cells were homogenized at about 4° C. in about 1 ml of about 0.1 M borate buffer (pH 8.8) containing about 2 mM mercaptoethanol. The homogenate was centrifuged at 4000 rpm for about 10 minutes at about 4° C. Protein concentration of the extracts was determined by the Bradford protein assay (BIO-RAD).

B. Chitooligosaccharides in combination with oligogalacturonans stimulate cell growth in Carrot cell suspension. This experiment was performed as described above, but using a Carrot (*Daucus carota*) cell suspension. The cell density was measured by weight (g of cell/mL).

Figure 4:
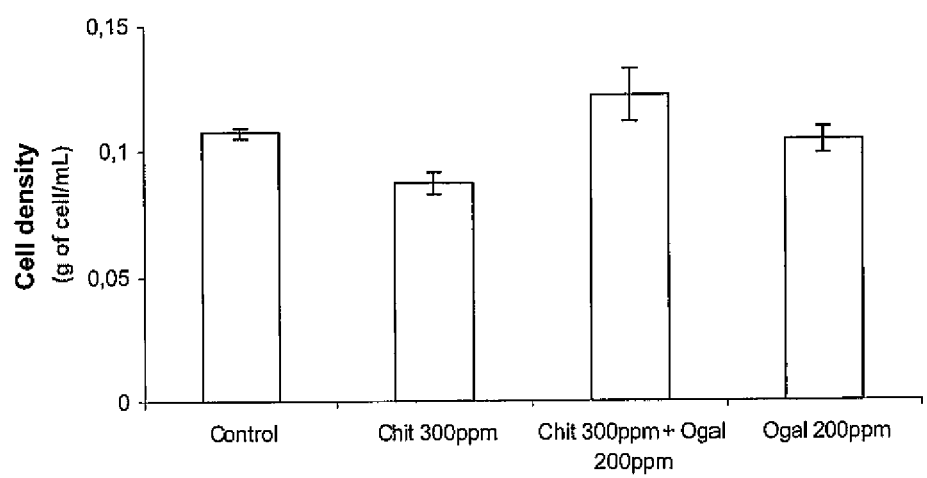
FIG. 4 is a representation of cell density of Carrot cell suspension after treatment with chitooligosaccharides, oligogalacturonans and their combination.

FIG. 4 represents the cell density of Carrot cell suspension 24 h after treatment with chitooligosaccharides (fully deacetylated, DP between 5 and 9), oligogalacturonans (DP higher than 8) and their combination. Data are mean±SD of triplicate samples from one representative of two independent experiments.

C. Specific combinations of oligogalacturonans and chitooligosaccharides have higher elicitor activity of plant defense reaction than individual oligosaccharides.

This experiment was performed as described above. PAL (EC 4.3.1.5) activity was determined in 0.125 ml supernatant in the presence of about 1.37 ml about 0.1 M borate buffer (pH 8.8) supplemented with about 60 mM L-Phenylalanine as described by Beaudoin-Eagan and Thorpe (Plant. Physiol 78: 438-441, 1985) and expressed as micromole of cinnamic acid produced per mg of protein per hour).

Figure 5:
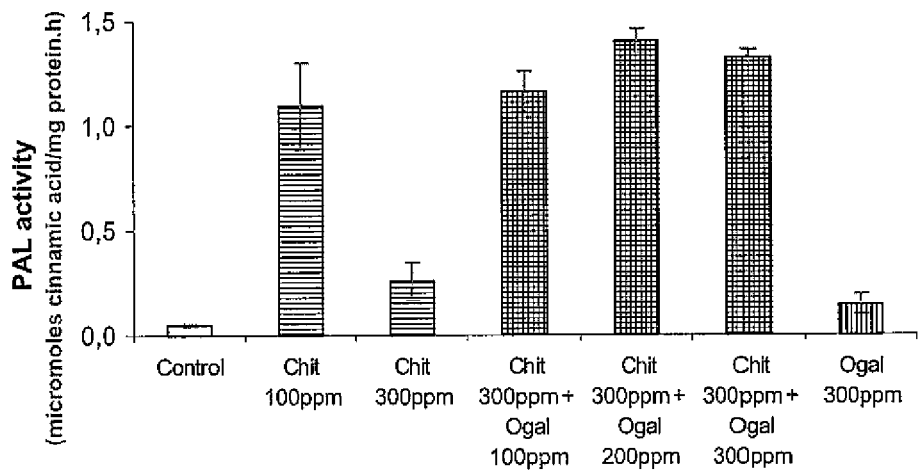
FIG. 5 is a graph of PAL activity in Arabidopsis cell suspension after treatment with chitooligosaccharides, oligogalacturonans and their combination.

FIG. 5 represents the induction of PAL activity in *Arabidopsis* cell suspension 24 h after treatment with chitooligosaccharides (fully deacetylated, DP between 5 and 9), oligogalacturonans (DP higher than 8) and their combination. Data are mean±SD of triplicate samples from one representative of two independent experiments.

D. Specific combinations of oligogalacturonans and chitooligosaccharides induce lower oxidative stress in plants than individual application of these oligosaccharides.

Cell culture conditions are similar to the ones described above.

$H_2O_2$ measurement: Chitooligosaccharides to be tested were dissolved in about 50 μL distilled water, filtered through a 0.22 μm membrane filter (MILLIPORE) and added to about 5 mL of 3 days-old suspension-cultured cells and incubated at 25° C. with shaking. Aliquots of about 100 μL were removed every 4 minutes during 30 minutes, quick spin centrifuged and the $H_2O_2$ concentration was measured in the supernatant using the Amplex Red hydrogen peroxide/Peroxidase Assay Kit (MOLECULAR PROBES) according to the supplier's instructions.

Figure 6:
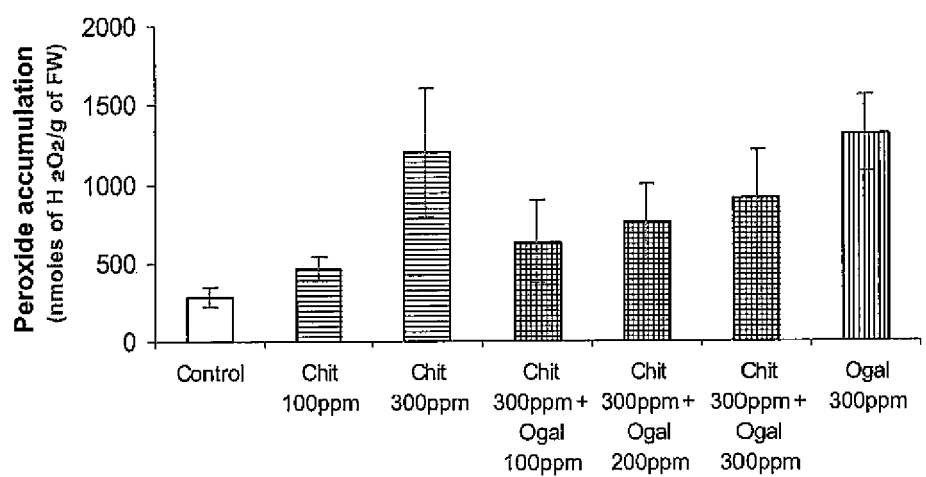
FIG. 6 is representation of the hydrogen peroxide accumulation in arabidosis cell suspension after treatment with chitooligosaccharides, oligogalacturonan and their combination.

FIG. 6 represents the hydrogen peroxide accumulation in *Arabidopsis* cell suspension 24 h after treatment with chitooligosaccharides (fully deacetylated, DP between 5 and 9), oligogalacturonan (DP higher than 8) and their combination. Data are mean±SD of triplicate samples from one representative of two independent experiments.

Example 5

Specific Combinations of Oligogalacturonides and Chitooligosaccharides can be Absorbed by Tomato Seeds and Stimulate Plant Growth Seeds of tomato (*Lycopersicum esculentum*) plant of the variety "Moneymaker" were immersed in a solution containing a mixture of oligogalacturonides and chitooligosacharides in ionic conditions adequate to induce pectic dimers formation ($Ca^{2+}/Na^+$ cations at about 0.5 mM $Ca^{2+}/150$ mM $Na^+$ ratio) or a solution containing all the elements of the mixture excluding the oligosaccharides mixture (Control) for 4 hours. The chitooligosaccharides used had a Degree of Acetylation of 25%. Then, the seeds were dried before planting and cultivated during 30 days in a 6-cavity seed bed in soil at 25° C. in a 16 h daylight/8 h dark regime.

Figure 7:
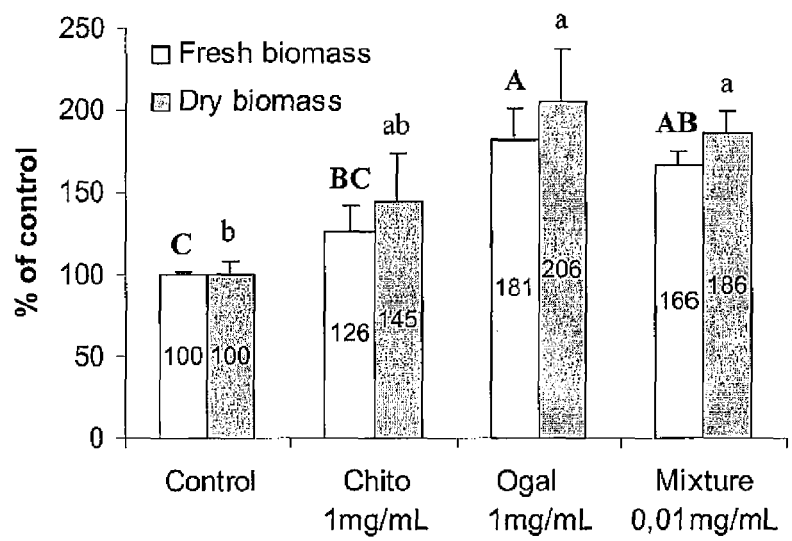
FIG. 7 is a representation of biomass (fresh and dry) of 30 day old tomato plants obtained from the seeds treated with chitooligosaccharides; oligogalacturonides and their combination, expressed as a percentage of biomass of control plants.

FIG. 7 represents the biomass (fresh and dry) of 30 day-old tomato plants obtained from the seeds treated with chitooligosaccharides, oligogalacturonides and their combination, expressed as percentage of the biomass of control plants. Values of the mean±SE are reported (n=3). Capital letters and small letters refer to two independent ANOVA tests. Data with the same letters are not statistically different (P<0.05).

Example 6

Foliar Application of Specific Combinations of Oligogalacturonides and Chitooligosaccharides Synergistically Induce Defense Reactions in Tomato Plants Tomato plants of the variety "moneymaker" were cultivated in soil under controlled conditions with a light/dark regime of 16 h/8 h respectively, at 25° C., during 20 days before being sprayed with solutions containing the mixture of oligogalacturonides and chitooligosachharides at 250 mg·L-1 dissolved in a solution at pH 5.5 containing Tween 20 at about 0.01% and $Ca^{2+}/Na^+$ cations at about 0.5 mM $Ca^{2+}/150$ mM $Na^+$ ratio. The chitooligomers used in the mixture had a Degree of Acetylation (DA) of 25%. As a control, water containing about 0.01% Tween 20 was sprayed on the leaves.

After 24 hours, the true leaves from plants treated by spraying were collected and ground in liquid nitrogen. Powdered leaves were extracted in 50 mM sodium acetate buffer pH 5.2 containing about 5 mM EDTA, about 14 mM β-mercaptoethanol and about 1.0 M NaCl to the rate of about 1 g of powdered leaves per 2 ml of buffer. The extract was then centrifuged at 12000 g for 15 minutes at 4° C. The supernatant was analyzed for activity of two Pathogenesis Related Proteins: glucanase (activity expressed as mg of glucose released/mg of protein·min) (Boudart et al. (1998) Planta 206:86-94) and chitinase (activity expressed as picomoles of p-nitrophenol released/mg protein·min) (Chitinase Assay kit, Sigma).

Figure 8:
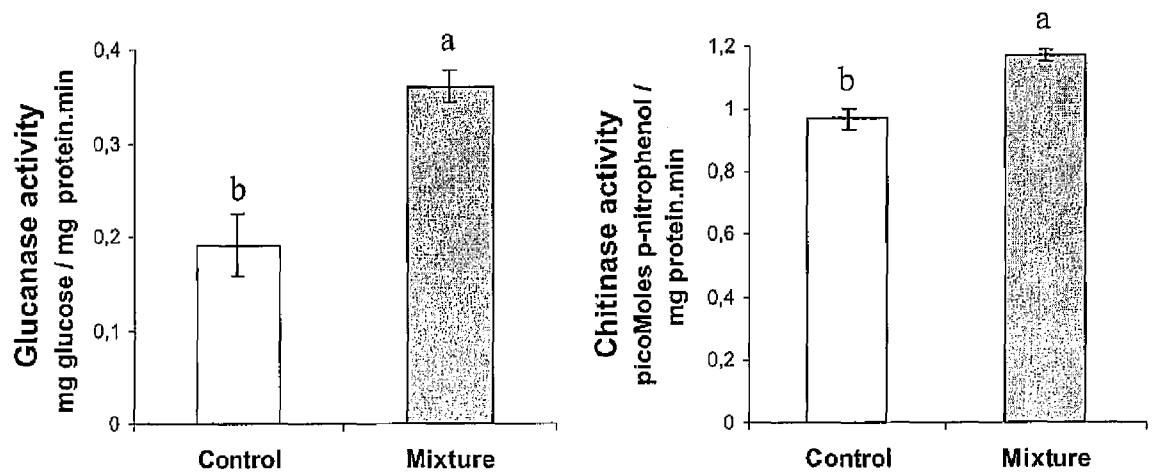
FIG. 8 is a representation of the induction of glucanase and chitinase activity in tomato plants after a foliar application of the mixture of oligogalacturonides and chitooligosaccharides.

FIG. 8 represents the induction of glucanase and chitinase activity in tomato plants after 24 hours of a foliar application of the mixture of oligogalacturonides and chitooligosaccharides. Values of the mean±SE are reported (n=3). ANOVA tests indicate statistically significant differences (P<0.05) between plants treated with the control solution and the mixture.

Example 7

Specific Combinations of Oligogalacturonides and Chitooligosaccharides Synergistically Induce Defense Reactions in *Arabidopsis* Plants

*Arabidopsis thaliana* plants were grown at 25° C. in a 16 h daylight/8 h dark regime, on semi-solid medium containing about 4.4 g/L Murashige and Skoog nutrients, about 30 g/L sucrose and about 0.3 g/L agar. Full-grown plants were removed from the medium, washed with about 0.05 M MES buffer at pH 5.7 and transferred to the same buffer with $Ca^{2+}/Na^+$ cations at the about 0.5 mM $Ca^{2+}/150$ mM $Na^+$ ratio, which contains oligogalacturonides (DP 9-20) alone, chitooligomers (DP 5-9, DA 25%) alone, or a mixture of oligogalacturonides and chitooligomers. The phenylalanine ammonia lyase (PAL) activity was tested 24 h later (micromoles of cinnamic acid produced/mg protein·h).

Figure 9:
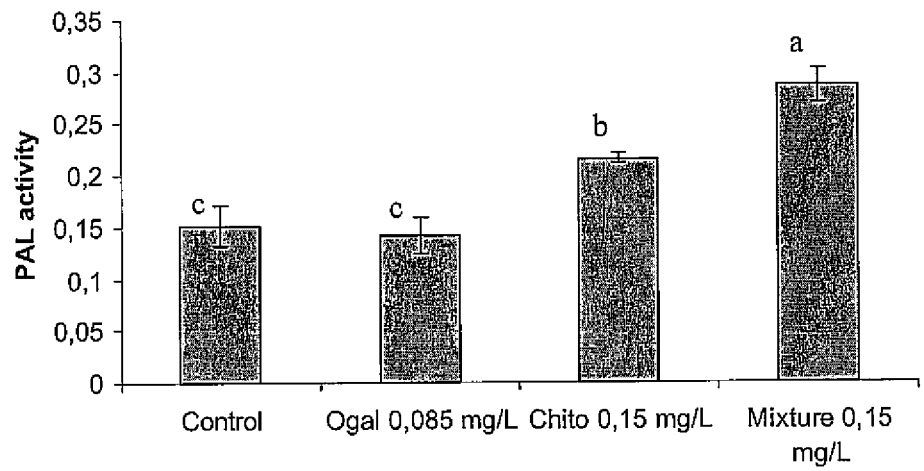
FIG. 9 is a representation of the induction of PAL activity in Arabidopsis plants treated with oligogalacturonides, chitooligomers of their combination.

FIG. 9 represents the induction of PAL activity in *Arabidopsis* plants treated with oligogalacturonides, chitooligomers or their combination. Values of the mean±SE are reported (n=3). ANOVA test indicates statistically significant differences (P<0.05) for plants treated with chitooligomers or mixture.

Example 8

Potassium Efflux and Medium Alkalinization

Suspension-cultured cells derived from leaves of *Arabidopsis thaliana* strain L-MM1 ecotype *Landsberg erecta* were grown in Murashige and Skoog medium (about 4.43 g $L^{-1}$) with sucrose (about 30 g $L^{-1}$), about 0.5 μg $mL^{-1}$ NAA, about 0.05 μg $mL^{-1}$ Kinetin, pH 5.7. Cultures were maintained under a 16 h/8 h light/dark photoperiod, at about 25° C., on a rotary shaker at 100 rpm. Cells were diluted 10-fold in fresh medium every seven days. Seven day-old cells were used for the experiments.

Chitooligosaccharides (about 30 mg $L^{-1}$), oligogalacturonides (about 40 mg $L^{-1}$) and a mixture of both oligosaccharides about 70 mg L-1 were dissolved in a solution containing about 10 mM sucrose, about 0.5 mM Ca2+, about 50 mM Na+, and about 0.5 mM MES adjusted to pH 5.7 with Tris-(hydroxymethyl)-aminomethane.

Aliquots of washed cells (100 mg Fresh Weight (FW) mL-1) were placed in glass vials and the incubation medium changed for equal volume of testing solutions and agitated on a rotatory shaker at 150 rpm. The extracellular pH and K+ concentrations were determined in aliquots of the incubation medium obtained by rapid filtration of the cells through Miracloth® (Calbiochem).

Extracellular pH changes were monitored with a pH electrode and extracellular K+ concentrations determined in 1N HCl using an atomic absorption spectrophotometer (PU 9200X, Pye-Unicam, Cambridge, UK).

Figure 10:
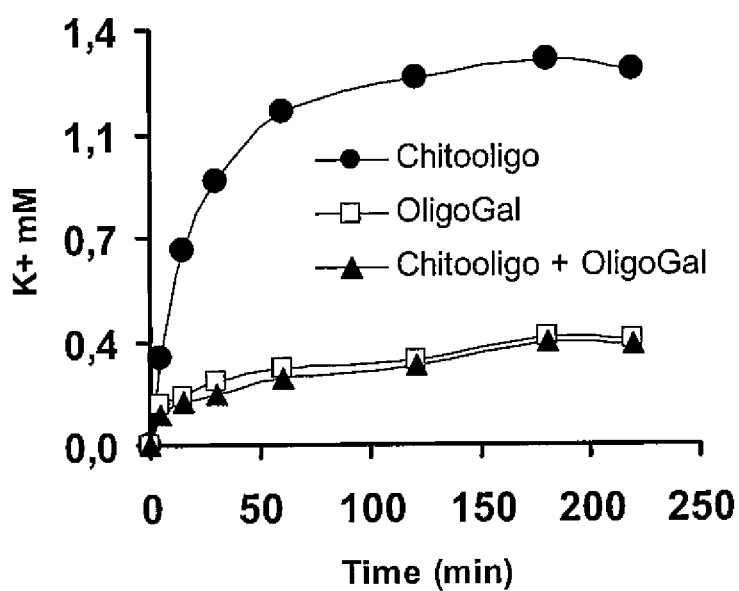
FIG. 10 is a representation of potassium efflux from Arabidopsis suspension cells treated with chitooligomers, oligogalacturonides or the mixture.

FIG. 10 shows potassium efflux from *Arabidopsis* suspension cells treated with chitooligomers, oligogalacturonides or the mixture. The mixture controls potassium efflux down to values similar to oligogalacturonides only.

Figure 11:
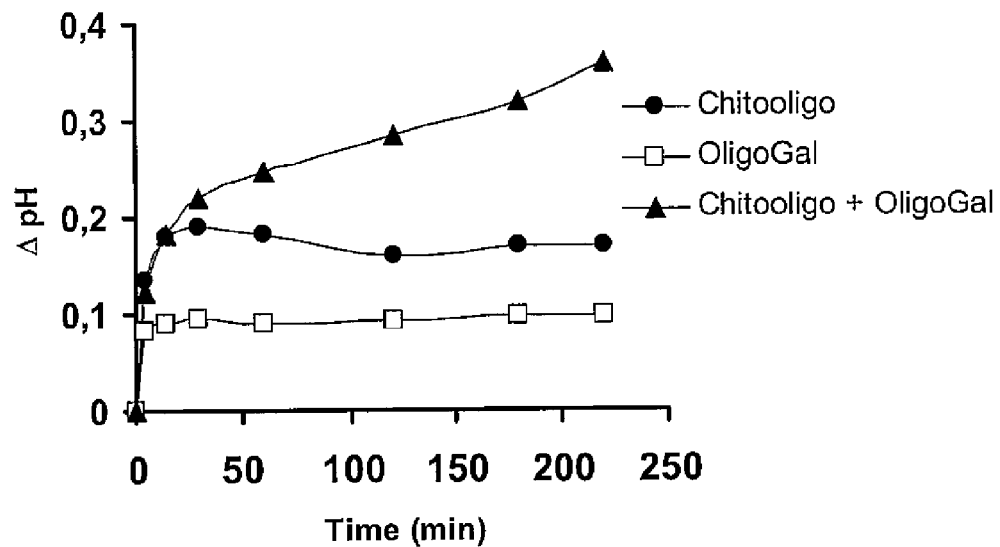
FIG. 11 is a representation of the medium alkalinization of Arabidopsis suspension cells treated with chitooligomers, oligogalacturonides or the mixture.

FIG. 11 shows the medium alkalinization of *Arabidopsis* suspension cells treated with chitooligomers, oligogalacturonides or the mixture. The mixture induces sustained medium alkalinization while individual components have an effect for less than one hour after treatment.

Figure 12:
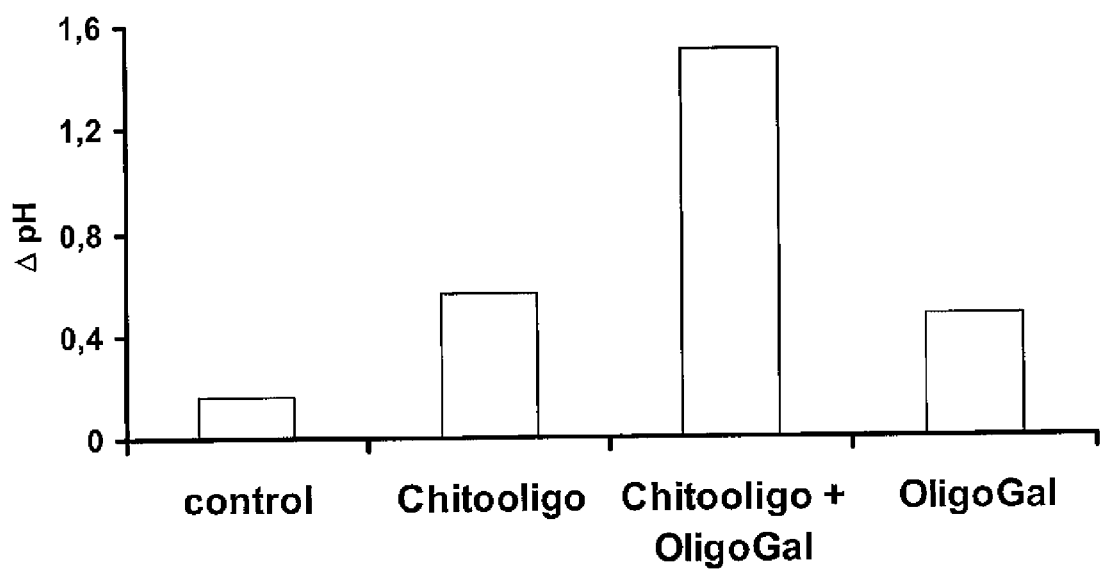
FIG. 12 is a representation of the medium alkalinization of Arabidopsis suspension cells after treatment with chitooligomers, oligogalacturonides or the mixture.

FIG. 12 represents the medium alkalinization of *Arabidopsis* suspension cells 24 h after treatment with chitooligomers, oligogalacturonides or the mixture. The mixture induces a clearly higher medium alkalinization than individual components.

Example 9

Proteomics/Genomics/Transcriptomics Analyses

For these analyses, cell cultures of *Arabidopsis thaliana* were conducted as described above.
A. Proteomic Analysis of Differentially Expressed Proteins.

After four hours of incubation with either control buffer, oligogalacturonans, oligochitosans or the mixture, the cells were harvested by centrifugation and the proteins were extracted and analyzed by two-dimensional gel electrophoresis using the protocol described by Valot et al. 2005 (Plant Molecular Biology 59: 565-580).

Proteomic analysis showed 59 significantly regulated proteins in at least one treatment in comparison to the three others. Among these 59 proteins, 44 were identified.

Over-expressed proteins were principally associated with defence mechanisms, like PAL (Phenylalanine Ammonia Lyase). It is interesting to see that one fourth of regulated proteins were related to energy metabolism. Remarkably, cluster analysis indicated that cells elicited with the bioactive mixture induced a pattern of soluble proteins expression different from the ones of cells elicited with single components that were more closely related to each other. Examples of proteins whose expression levels are different between treatments are represented in Table 2:

TABLE 2

|  | Control | Chitooligo-saccharides | Composition | Oligo-galacturonans |
|---|---|---|---|---|
| Succinate dehydrogenase | 1.00* | 2.00* | 0.93 | 1.53 |
| WD40-repeat protein | 1.00 | 0.75* | 1.12* | 0.85 |
| NADP dependent malic enzyme | 1.00 | 1.14* | 0.71* | 0.82 |
| Mitochondrial phosphate translocator | 1.00 | 0.88* | 1.51* | 1.12 |
| Glyceraldehyde-3-phosphate dehydrogenase (GAPDH) | 1.00* | 1.62* | 1.13 | 1.56 |

Proteins whose expression levels are statistically different from each other are marked by an asterisk (*).
B. Transcriptomic Analysis of Differentially Expressed Genes.

Transcriptomic analysis was carried out by cDNA microarray technique on *Arabidopsis* cells sampled four hours after treatment with elicitors. Total RNA from *Arabidopsis* treated cells were extracted using the QIAGEN RNeasy Mini Kit (Darlington Lab).

*Arabidopsis* transcriptomic analysis showed 96 significantly regulated genes (P<0.05) with at least a ratio of 3 fold, in at least 2 of the 3 treatments (oligogalacturonides, chitooligosaccharides, mixture of both). In contrast to the proteomic analysis, the transcriptomic analysis revealed that treatment of cultured cells with chitosan oligomers or with the mixture induced very similar response. Treatment with pectin oligomers seems to induce a limited response, close to control cultures. Treatments with chitosan oligomers, pectin oligomers or with their mixture regulate the expression of 95 (57 down, 38 up), 25 (16 down, 9 up) and 92 (56 down, 36 up) genes, respectively.

Among the regulated genes, several exhibit distinct expression patterns depending on the treatment. Some of those genes are listed in Table 3, where the levels of gene expression are given as ratio over the expression level in the control. Statistically significant differences are indicated by an asterisk.

TABLE 3

| name | Access # | Chitooligo-saccharides | compo-sition | Oligo-galacturonans |
|---|---|---|---|---|
| Clavata3/ESR-Related-1 | At1g73165 | −3.60* | −1.15 | 3.35* |
| proline-rich extensin-like family | At5g49080 | 3.15 | 2.51* | −3.68* |

TABLE 3-continued

| name | Access # | Chitooligo-saccharides | composition | Oligo-galacturonans |
|---|---|---|---|---|
| WD-40 repeat family protein | At5g40880 | 3.38* | 1.77 | −2.24* |
| defense-related protein | At3g44870 | 5.46* | −2.06* | −1.15 |
| co-chaperone grpE family | At4g26780 | −1.15 | 3.16* | 1.03 |
| AMP-binding protein | At1g75960 | 1.61 | 3.87* | 1.95 |

Example 10

Induction of Resistance to *Venturia inequalis* in Apple Seedlings

Apple seeds (approx. 1400), variety <<Golden Delicious>> were put to vernalize for 90 or 120 days at 4° C. after disinfection with bleach. Seeds were then sowed in topsoil at a density of 40 seeds per bed. Each bed was then covered with topsoil, watered and incubated at a temperature close to 10° C. for a week before being transferred in greenhouse at 18° C.

Figure 13:
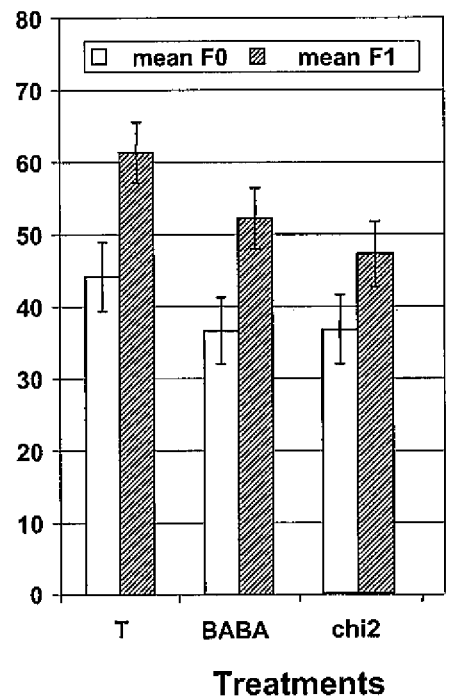
FIG. 13 is a representation of percent of sporulating leaf surface for the last leaf developed after treatment with elicitors and for the first leaf developed after treatment with elicitors.

Groups of 40 seedlings were treated by spraying with either a control solution (water plus 0.01% Tween 20) or elicitors in aqueous solutions (composition of the invention at 0.25 g·L-1 at the "3-leaves stage" at 10 and 3 days before inoculation with *Venturia inequalis* (150,000 viable conidia per mL). The percentage of sporulating surface area was evaluated 14 days after inoculation on the last leaf developed before treatment with elicitors (F1) and the first leaf developed after treatment with elicitors (F0). Results are expressed as percent of sporulating leaf surface area (mean±SD of 200 seedlings per treatment) for F1 and F0 as shown in FIG. 13.

Example 11

Figure 14:
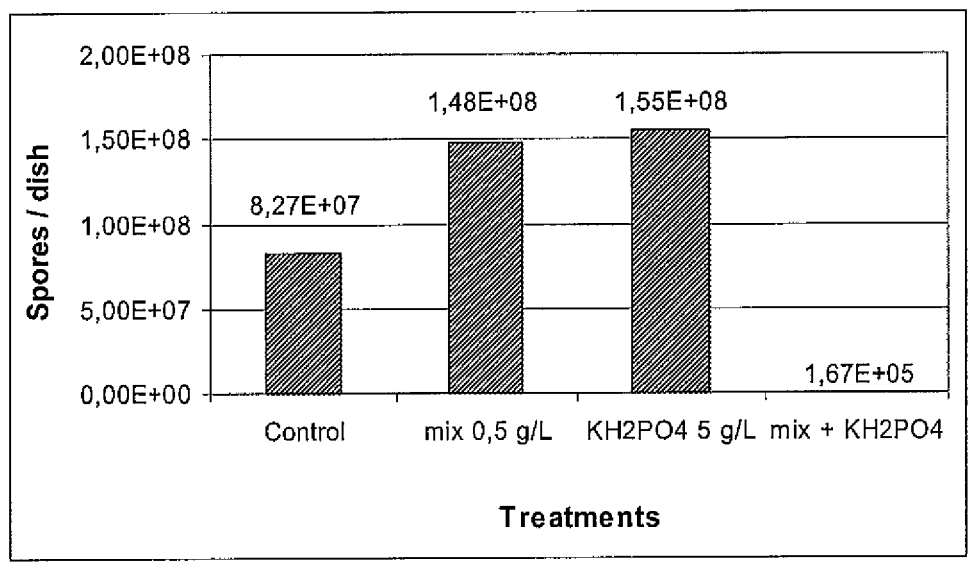
FIG. 14 is a representation of the resulting spores expressed as averages of 3 experiments for Example 11.

Fungicidal Properties of the Combination of $KH_2PO_4$ with a Mixture of Oligogalacturonides and Chitooligosaccharides Three 20 μl spots containing $2.10^4$ spores each of *Penicilium expansum* were inoculated on Petri dishes of 39 g·L$^{-1}$ Potato Dextrose Agar (PDA) spread with one of the following solutions: water+0.01% Tween 20 (control), mixture of oligogalacturonans and oligochitosans (0.5 g·L$^{-1}$), $KH_2PO_4$ g·L$^{-1}$), mixture of oligogalacturonans and oligochitosans (0.5 g·L$^{-1}$)+$KH_2PO_4$ (5 g·L$^{-1}$). The Petri dishes are incubated 48 h at 25° C. and the resulting spores are counted using a Neubauer cell. Results, expressed as averages of 3 experiments, are shown on FIG. 14.

The invention claimed is:

1. An aqueous solution comprising one or more oligogalacturonan(s) with a degree of polymerization comprising between 9 and 20 and having a dimeric egg box conformation stabilized by one or more chitosan oligosaccharide, wherein the aqueous solution does not form a gel.

2. The solution according to claim 1, wherein the chitosan oligosaccharide comprises a degree of polymerization higher than 5.

3. The solution according to claim 1, wherein the chitosan oligosaccharide comprises a degree of acetylation lower than 50%.

4. The solution according to the claim 1, further comprising one or more element(s) selected from the group consisting of other saccharides, growth regulators or growth factors, minerals, ions, nutriments, food additives, flavourings, colours, vitamins, phytonutrients, KH2PO4 and a bioactive molecule.

5. The solution according to the claim 1, further, comprising a product selected from the group consisting of a pharmaceutical composition, a nutraceutical composition, a food or feed composition including a functional food or a functional feed, a phytosanitary product, a fertilizer, an adjuvant of these products, a phytohormone replacement, a phytohormone enhancement, and a phytohormone modulator.

6. The solution of claim 5, wherein the phytosanitary product is a fungicide.

7. The solution of claim 1, comprising an anti-fungal adjuvant.

8. A method to induce protection of a plant against infection by plant pathogens, which comprises the step of adding the composition of claim 1 to a plant.

9. A fertilization method which comprises the step of adding the solution of claim 1 to a plant or to a plant seed.

10. A method of wound healing treatment, which comprises the step of administrating the solution of claim 1 to a subject having a wound in need of healing treatment.

* * * * *